(12) United States Patent
Hamilton et al.

(10) Patent No.: US 7,972,388 B2
(45) Date of Patent: Jul. 5, 2011

(54) METHODS AND KITS FOR MAINTAINING THE CONDITION OF COLORED HAIR

(75) Inventors: Carol Hamilton, New York, NY (US); Francois Cottard, Courbevoie (FR); Caroline Goget, Paris (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 12/679,572

(22) PCT Filed: Oct. 27, 2008

(86) PCT No.: PCT/US2008/081257
§ 371 (c)(1),
(2), (4) Date: Jun. 9, 2010

(87) PCT Pub. No.: WO2009/058701
PCT Pub. Date: May 7, 2009

(65) Prior Publication Data
US 2010/0254924 A1    Oct. 7, 2010

Related U.S. Application Data

(60) Provisional application No. 60/983,700, filed on Oct. 30, 2007.

(51) Int. Cl.
*A61Q 5/10* (2006.01)
*A61K 8/00* (2006.01)

(52) U.S. Cl. ............. 8/405; 8/408; 8/431; 8/485; 8/504; 8/521; 8/542; 8/552; 8/632; 132/202; 132/208; 424/70.1

(58) Field of Classification Search ............... 8/405, 408, 8/431, 485, 504, 521, 542, 552, 632; 132/202, 132/208; 424/70.1
See application file for complete search history.

(56) References Cited

U.S. PATENT DOCUMENTS

| | | | |
|---|---|---|---|
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Lowe et al. | |
| 6,099,592 A | 8/2000 | Vidal et al. | |
| 6,824,764 B2 * | 11/2004 | Devin-Baudoin et al. | ... 424/70.1 |
| 7,056,497 B2 | 6/2006 | Lenzi-Brangi et al. | |
| 7,232,466 B2 | 6/2007 | Narasimhan et al. | |
| 2003/0113280 A1 | 6/2003 | Kleen | |
| 2004/0089316 A1 | 5/2004 | Hamilton et al. | |
| 2004/0244126 A1 | 12/2004 | Vena et al. | |
| 2007/0169285 A1 | 7/2007 | Narasimhan et al. | |
| 2007/0220684 A1 | 9/2007 | Narasimhan | |

FOREIGN PATENT DOCUMENTS

| | | |
|---|---|---|
| DE | 3843892 | 6/1990 |
| DE | 4133957 | 4/1993 |
| DE | 195 43 988 | 5/1997 |
| FR | 2 733 749 | 11/1996 |
| GB | 1026978 | 4/1966 |
| GB | 1153196 | 5/1969 |
| WO | WO 94/08969 | 4/1994 |
| WO | WO 94/08970 | 4/1994 |

OTHER PUBLICATIONS

International Preliminary Report on Patentability dated May 14, 2010 in corresponding International Application No. PCT/US2008/081257.

International Search Report and Written Opinion of the International Searching Authority in corresponding International Application No. PCT/US2008/081257.

\* cited by examiner

*Primary Examiner* — Eisa B Elhilo
(74) *Attorney, Agent, or Firm* — Maria Luisa Balasta; Steven Trzaska

(57) ABSTRACT

The present invention provides for kits and methods of treating hair in order to inhibit color fading and/or impart both shine- and condition-enhancing properties to colored hair, comprising a pre-treatment composition, a color-altering composition, a developer composition, a shampoo composition, a conditioner composition, and a post-treatment composition, wherein the post-treatment composition contains at least about 5% by weight of at least one oily component, based on the total weight of the post-treatment composition.

16 Claims, No Drawings

METHODS AND KITS FOR MAINTAINING THE CONDITION OF COLORED HAIR

STATEMENT OF RELATED APPLICATIONS

This application is a national phase of PCT/US08/81257, filed on Oct. 27, 2008 which claims priority to U.S. Provisional Application No. 60/983,700, filed Oct. 30, 2007, the entire contents of all are hereby incorporated by reference.

BACKGROUND OF THE INVENTION

There are several methods of altering the color of hair. These methods generally require the use of an alkaline agent (such as ammonia), an oxidizing agent (such as hydrogen peroxide), and optionally, a dye or colorant. The reaction of these components with the hair results in weakening the mechanical attributes of the hair fiber, increases the porosity of the fiber, and in general results in hair that is severely dry and damaged. Additionally, the color that has been deposited often fades with time due to washing or upon exposure to environmental factors such as sun, humidity, and pollution. This leads to a brassy, dull appearance and results in more frequent re-coloring than desired, which may result in less conditioned hair. In order to inhibit color fading and preserve the condition of colored treated hair, a specialized hair care regimen is required.

Many at-home hair coloring, bleaching, or highlighting products offer multiple-part kits that contain separate solutions of an after-color shampoo or conditioning treatment to repair the hair immediately following coloration. However, a drawback of these kits is that they are incomplete in the range of products needed to care for color treated hair. Merely one shampoo or conditioning treatment is not sufficient to moisturize and maintain the quality of colored treated hair. This is particularly evident for those who bleach their hair, since higher volumes of hydrogen peroxide are needed for additional lightening, which consequently results in greater damage to the hair. The consumer may thus be left feeling bewildered with what further care is necessary to preserve the quality of their color treated hair and inhibit color fading.

There is thus a need for a hair coloring kit that is easy to use such that a consumer is able to provide a specialized care regimen to preserve the condition of their color treated hair and inhibit color fading. This is done by providing in one kit all the components needed to maintain and care for the hair for several weeks following hair coloration.

BRIEF SUMMARY OF THE INVENTION

A method of treating the hair, comprising:
a) applying a pre-treatment composition to the hair;
b) combining a color-altering composition and a developer composition to form a mixture;
c) applying the mixture onto the hair;
d) removing said mixture from the hair;
e) washing the hair with a shampoo composition;
f) conditioning the hair with a conditioner composition; and,
g) applying a post-treatment composition onto the hair in order to inhibit color fading and/or impart both shine- and condition-enhancing properties, and wherein the post-treatment composition contains at least about 5% by weight of at least one oily component, based on the total weight of the post-treatment composition.

A hair care kit, comprising:
a) a compartment containing a pre-treatment composition;
b) a compartment containing a color-altering composition;
c) a compartment containing a developer composition;
d) a compartment containing a shampoo composition;
e) a compartment containing a conditioner composition; and,
f) a compartment containing a post-treatment composition, wherein the post-treatment composition contains at least about 5% by weight of at least one oily component, based on the total weight of the post-treatment composition.

DETAILED DESCRIPTION OF THE INVENTION

Other than in the operating examples, or where otherwise indicated, all numbers expressing quantities of ingredients or reaction conditions are to be understood as being modified in all instances by the term "about".

In accordance with the invention there may be provided a hair care kit. As used herein, the term "kit" broadly includes items that are either sold or packaged together. While the kit may be distributed to end users through salons, one aspect of the invention involves distributing kits to consumers through retail sales channels such as drugstores, department stores, grocery stores, and cosmetic stores, on-line stores, and other retail or user accessible discount or wholesale chains. This aspect of the invention may permit consumers to purchase the product for home use.

As used herein, the term "compartment" refers to any receptacle, regardless of shape, material, or closure, which serves a containing function. For example, the term "compartment" as used throughout, broadly includes, (but is not limited to) the interior of a tube, sack, canister, can, tub, bottle, jar, packet, carton, box, envelope, or any other vessel. Components may be contained in a single receptacle, or may be divided amongst multiple receptacles.

As used herein, the term "color-altering" composition refers to any composition which changes or enhances the color of the hair. Examples of such compositions include coloring compositions containing oxidative and/or direct dyes, bleaching compositions, and/or highlighting compositions.

I. Kits, Compartments, and Compositions

A. Color-Altering Composition

In accordance with the invention, the kit may include at least one compartment containing a color-altering composition. The color-altering composition may comprise a hair dye material and/or a bleaching material.

1. Dye Material

The hair dye material may be chosen from primary intermediates and couplers.

i). Primary Intermediates

Suitable primary intermediates are well known for use in hair color, and include ortho or para substituted aminophenols or phenylenediamines, double bases, bis(phenyl)alkylene-diamines, heterocyclic bases, and the acid addition salts thereof.

Among the para-phenylenediamines, mention may be made of para-phenylenediamine, 2-methyl-para-phenylenediamine, 1-(N-ethyl-N'-β-hydroxyethyl)-amino-4-aminobenzene, 1-N,N'-bis(β-hydroxyethyl)amino-4-aminobenzene, 1-N,N'-bis(β,γ-dihydroxypropyl)amino-4-aminobenzene, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-amino-N,N-diethyl-2-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-carbamylmethylaniline, 4-amino-3-methyl-N-ethyl-N-carbamylmethylaniline, 4-amino-N-ethyl-N-(β-piperidinoethyl)aniline, 4-amino-3-methyl-N-ethyl-N-(β-piperidinoethyl)aniline, 4-amino-N-ethyl-N-(β-morpholinoethyl)aniline, 4-amino-3-methyl-N-ethyl-N-(β-morpholinoethyl)aniline, 4-amino-ethyl-N-(β-acetylaminoethyl)aniline, 4-amino-N-(β-methoxyethyl)aniline, 4-amino-3-methyl-N-ethyl-N-(β-acetylaminoethyl)aniline, 4-amino-N-ethyl-N-(β-mesylaminoethyl)aniline, 4-amino-3-methyl-N-ethyl-N-(β-mesylaminoethyl)aniline, 4-amino-N-ethyl-N-(β-sulphoethyl)aniline, 4-amino-3-methyl-N-ethyl-N-(β-sulphoethyl)aniline, N-[4'-(amino)phenyl]morpholine, N[4'-(amino)phenyl]piperidine, N-(4'-aminophenyl)-para-phenylenediamine, N-phenyl-para-phenylenediamine, 2-fluoro-para-phenylenediamine, 2-carboxy-para-phenylenediamine, 2-sulpho-para-phenylenediamine, 2-isopropyl-para-phenylenediamine, N-(β hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, 2-β-hydroxyethyloxy-para-phenylenediamine, 2-β-acetylaminoethyloxy-para-phenylenediamine, N-β-methoxyethyl-para-phenylenediamine, para-toluylenediamine, 2-n-propyl-para-phenylenediamine, 1,β-methoxyethylamino-4-aminobenzene, 4-aminophenyl 1-(3-hydroxy)pyrrolidone, and acid addition salts thereof.

Among the ortho-phenylenediamines, mention may be made of N1-(2-Hydroxyethyl)-4-Nitro-o-Phenylenediamine, 4-Methyl-o-Phenylenediamine, and 4-Nitro-o-Phenylenediamine and acid addition salts thereof.

As used herein, the term double bases means compounds comprising at least two aromatic nuclei having at least one of amino and hydroxyl groups.

Among the double bases that can be used as oxidation bases in the dye compositions disclosed herein, mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium, and ammonium radicals. Mention may also be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as oxidation bases in the dye compositions in accordance with certain embodiments, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Among the pyrazole and pyrazolinone derivatives, mention may be made the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 2-(4,5-diamino-1H-pyrazol-1-yl), $H_2SO_4$, 2,3-diamino-6,7-dihydro-1H,5H-pyrazolo[1,2-z]pyrazol-1-one, 1-methyl-3-phenyl-2-pyrazolinone, and the acid addition salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

When they are present, the primary intermediates may be employed in amounts ranging from at least about 0.001 to 10% by weight, preferably at least about 0.005 to 10% by weight, and more preferably at least about 0.005 to 6% by weight, based on the total weight of the color-altering composition.

ii). Coupler

The couplers that may be used in the dyeing method disclosed herein include those conventionally used in oxidation dye compositions, that is to say, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the general formula:

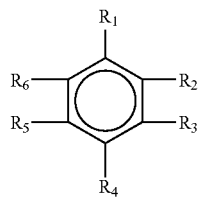

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(3-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1, 2,4-triazole, 2,6-dimethylpyrazolo[1,5-b]-1,2,4-triazole, 6-methyl pyrazolo[1,5-a]-benzimidazole, and the acid addition salts thereof.

In general, the acid addition salts of the oxidation bases and couplers may be chosen from hydrochlorides, hydrobromides, sulphates, tartrates, lactates, and acetates.

Preferred couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyethylaminophenol, 6-hydroxyindole, 2-amino-3-hydroxypyridine, 5-amino-6-chloro-o-cresol, their salts, or mixtures.

When they are present, the couplers may be employed in amounts ranging from at least about 0.001 to 10% by weight, preferably at least about 0.005 to 10% by weight, and more preferably at least about 0.005 to 6% by weight, based on the total weight of the color-altering composition.

According to an exemplary aspect, the salts which can be cosmetically used in the context of the composition of the invention for oxidation bases and the couplers present may be chosen from the addition salts with an acid such as the hydrochlorides, hydrobromides, sulfates, citrates, succinates, tartrates, lactates, tosylates, benzenesulfonates, phosphates and acetates, for example, and the addition salts with a base such as sodium hydroxide, potassium hydroxide, aqueous ammonia, amines or alkanolamines, for example.

In yet another exemplary embodiment, the dye material may comprise one or more direct dyes, disperse dyes, basic dyes, HC dyes, and acid dyes.

The appropriate medium for dyeing, also called dye carrier, may include water or a mixture of water and at least one organic solvent to solubilize the compounds which might not be sufficiently soluble in water. By way of organic solvent, suitable examples may be chosen from $C_1$-$C_4$ lower alkanols, such as ethanol and isopropanol; for example, polyols and polyol ethers such as 2-butoxyethanol, propylene glycol, propylene glycol monomethyl ether, diethylene glycol monoethyl ether and monomethyl ether, for example, and aromatic alcohols such as benzyl alcohol or phenoxyethanol, for example, and mixtures thereof. Other examples of solvents for use in the present invention are hexyleneglycol and dipropylene glycol, and mixtures thereof.

II. Bleaching Material

As with the hair dye material, the hair bleaching material may be completely contained within a single compartment (as defined previously) or may be contained within multiple compartments.

In a broad sense, the hair bleaching material may be any ingredient or combination of ingredients for adding a tone to the hair. While the invention, in its broadest sense, is not limited to any particular bleaching formulation or compound, one suitable example includes a two component bleaching formulation, mixed, prior to application, by the user. The bleaching material may be chosen from alkali metal salts and inorganic peroxygenated salts, such as sodium or ammonium or potassium persulfates, perborates, and percarbonates. The colorant composition containing bleaching material may be in powder cream, paste, oil, or gel form.

When they are present, the bleaching material may be employed in amounts ranging from at least about 5 to 70% by weight, preferably at least about 10 to 65% by weight, and more preferably at least about 15 to 60% by weight, based on the total weight of the color-altering composition.

The color-altering compartment may further comprise an alkalinizing agent. Suitable alkalinizing agents may be chosen, by way of example, from aqueous ammonia, alkali metal carbonates, alkanolamines such as mono-, di- and triethanolamines and derivatives thereof, sodium or potassium hydroxides and the compounds having the following formula:

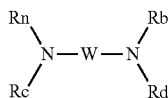

in which W is a propylene residue which is optionally substituted with a hydroxyl group or a $C_1$-$C_4$ alkyl radical; $R_a$, $R_b$, $R_c$ and $R_d$, which are identical or different, represent a hydrogen atom, a $C_1$-$C_4$ alkyl or $C_1$-$C_4$ hydroxyalkyl radical.

In an exemplary embodiment, the color-altering compartment may further comprise various adjuvants conventionally used in compositions for dyeing hair, such as, for example, anionic, cationic, nonionic, amphoteric or zitterionic agents, or mixtures thereof, anionic, cationic, nonionic, amphoteric or zitterionic polymers, or mixtures thereof, inorganic or organic thickening agents, and in particular anionic, cationic, nonionic and amphoteric associative polymeric thickeners, antioxidants, penetrating agents, sequestrants, perfumes, buffers, dispersing agents, conditioning agents such as, for example, volatile or nonvolatile, modified or unmodified silicones, film-forming agents, ceramides, preservatives, and opacifying agents. Persons skilled in the art may choose this or these possible additional compounds such that advantageous properties which may be intrinsically attached to the oxidation dyeing composition in accordance with the invention may not, or may not substantially, be impaired by the addition(s) envisaged.

The pH of the color-altering compartment in accordance with an exemplary aspect of the invention may range from about 3 to about 12, and/or from about 5 to about 11, for example. The pH may be adjusted to the desired value by means of acidifying or alkalinizing agents customarily used in dyeing keratinous fibres or alternatively using conventional buffer systems.

Suitable acidifying agents may be chosen, for example, from inorganic or organic acids, such as hydrochloric acid, orthophosphoric acid, sulphuric acid, carboxylic acids, such as acetic acid, tartaric acid, citric acid, lactic acid, for example, and sulphonic acids.

2. Developer Compartment

The kit may include at least one compartment containing a developer composition. In the claimed method, the color-altering composition is mixed with the developer composition to activate the dye or bleaching composition so that it is suitable to color the hair. The developer composition, in its simplest form, is an aqueous solution of hydrogen peroxide. Developer compositions are generally sold in the form of 10, 20, 25, and 30 volume hydrogen peroxide. The 25 volume hydrogen peroxide developer composition contains about 7.5% by weight of the total composition of hydrogen peroxide. The 30 volume hydrogen peroxide developer composition contains about 9% by weight of the total composition of hydrogen peroxide. Other suitable oxidizers may be chosen from urea peroxide, melamine peroxide, persulfates, perborates and percarbonates such as sodium perborate or percarbonate.

If desired, the developer composition may contain a variety of other ingredients known in the industry that enhance the aesthetic properties and contribute to more efficient coloring of hair, such as oils, surfactants, humectants, and preservatives.

3. Pre-Treatment Compartment

The kit may include at least one compartment containing a pre-treatment composition. This composition may comprise organic oils, esters, humectants, nonionic surfactants, cationic conditioning agents, plant extracts, vitamins, and natural and synthetic oils at levels that are suitable in the industry.

i). Organic Oils

Suitable organic oils include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like.

The organic oil may also comprise glyceryl esters of fatty acids, or triglycerides, such as castor oil, lanolin oil, triisocetyl citrate, $C_{10-18}$ triglycerides, caprylic/capric/triglycerides, coconut oil, mineral oil, almond oil, apricot kernel oil, avocado oil, babassu oil, evening primrose oil, *camelina sativa* seed oil, grape seed oil, *macadamia ternifolia* seed oil, corn oil, meadowfoam seed oil, mink oil, olive oil, palm kernel oil, safflower oil, sesame oil, soybean oil, sunflower oil, wheat germ oil, *camellia reticulata* seed oil and the like.

Also suitable as the oil are glyceryl esters (excluding fats and oils which are glyceryl esters of fatty acids) which are primarily fatty acid mono- di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the organic oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the oil are various fluorinated oils are fluoro guerbet esters or perfluropolyethers.

Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

ii). Humectants

Suitable humectants include glycerin, propylene glycol, butylene glycol, ethylene glycol, polyethylene glycols having from 4 to 250 repeating ethylene glycol units, ethoxydiglycol, and the like.

iii). Nonionic Surfactants

Non-limiting examples of non-ionic surfactants may include alkoxylated derivatives of the following: fatty alcohols, alkyl phenols, fatty acids, fatty acid esters and fatty acid amides, wherein the alkyl chain is in the $C_{12-50}$ range, typically in the $C_{16-40}$ range, more typically in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Commercially available nonionic surfactants are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_6$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other non-ionic surfactants suitable for use in the present invention are glyceryl esters and polyglyceryl esters, including but not limited to, glyceryl monesters, typically glyceryl monesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being typical. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to 20).

iv). Conditioners

A variety of conditioners are suitable, including cationic quaternary ammonium compounds, amide or amine conditioning agents, and cationic polymers.

(a). Cationic Quaternary Ammonium Compounds

Suitable cationic conditioning agents include cationic quaternary ammonium salts. Examples of such salts include those having the formula:

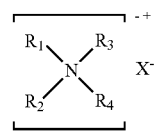

wherein $R_1$ is an aliphatic group of 1 to 22 carbon atoms, or aromatic, aryl, or alkaryl group having 12 to 22 carbon atoms; $R_2$ and $R_3$ are each independently an aliphatic group having 1-22 carbon atoms; and $R_4$ is an alkyl group of from 1 to 3 carbon atoms, and X is an anion selected from halogen, acetate, phosphate, nitrate and methyl sulfate radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, Other quaternary ammonium salts that may be used as a conditioning agent include compounds of the general formula:

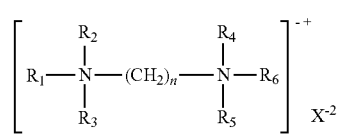

wherein $R_1$ is an aliphatic group having 16 to 22 carbon atoms, $R_2$, $R_3$, $R_4$, $R_5$, and $R_6$ are the same or different and are selected from alkyls having 1 to 4 carbon atoms and X is an anion as above defined.

Also, quaternary imidazolinium salts having the following general formula are suitable as conditioning agents:

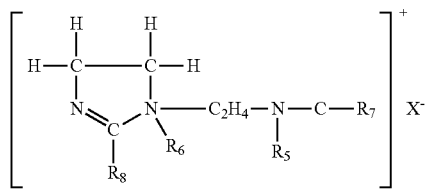

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

(b). Amide or Amine Conditioning Agents

Amides which exhibit the general formulas set forth below are also suitable conditioning agents:

wherein R is a straight or branched chain saturated or unsaturated alkyl having 6 to 30 carbon atoms, n is an integer from 1 to 4, and X and Y are each independently H, or $C_{1-6}$ lower alkyl. Preferred is an Amide of the Formula:

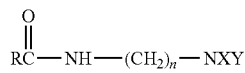

wherein R is a $C_{12-22}$ straight or branched chain alkyl, n is an integer from 1 to 4, and X is lower alkyl, preferably methyl.

Also suitable are amidoamine salts, which are the condensation products of fatty acids with a polyfunctional amines, for example, those having the formula $RCONH(CH_2)_n NR_1R_2$ where RCO is a fatty acyl group such as stearoyl, $R_1$ and $R_2$ are methyl or ethyl, and n is 2 or 3. Examples of such compounds include stearmidopropyl dimethylamine. Particularly preferred are amidoamine compounds complexed with a mild dimer acid, such as di(behenamidopropyl dimethyl amine)dimer dilinoleate or di(linoleamidopropyl dimethyl amine)dimer linoleate. Both ingredients are sold by Alzo, Inc. under the NECON tradename.

Also suitable are salts of fatty primary, secondary, or tertiary amines, wherein the substituted groups have 12 to carbon atoms. Examples of such amines include dimethyl stearamine, dimethyl soyamine, stearylamine, myristylamine, tridecylamine, ethyl stearamine, and so on.

(c). Cationic Polymers

Also suitable as conditioning agents are a variety of cationic polymers including but not limited to those set forth below:

1. Quaternized Cellulose Ethers

Suitable conditioning agents include quaternary derivatives of cellulose ethers such as polymers sold under the tradename JR-125, JR-400, JR-30M.

2. Copolymers of Vinyl Pyrrolidone

Copolymers of vinylpyrrolidone are suitable conditioning agents, including but not limited to those having monomer units of the formula:

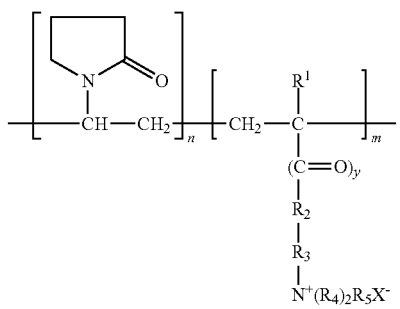

wherein $R^1$ is hydrogen or methyl, preferably methyl;
y is 0 or 1, preferably 1
$R^2$ is 0 or NH, preferably NH;
$R^3$ is $C_xH_{2x}$ where x is 2 to 18, or —$CH_2$—CHOH—$CH_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

3. Acrylic Polymers

Suitable conditioning agents also include homopolymers of dimethyldiallylammonium chloride, or copolymers of dimethyldiallylammonium chloride and acrylamide. Such compounds are sold under the tradename MERQUAT by Merck. Also suitable are various types of homo- or copolymers derived from acrylic or methacrylic acid, selected from monomer units acrylamide, methylacrylamide, diacetoneacrylamide, acrylamide or methacrylamide substituted on the nitrogen by lower alkyl, alkyl esters of acrylic acid and methacrylic acid, vinylpyrrolidone, or vinyl esters.

4. Shampoo Compartment

The kit may include at least one compartment containing a shampoo composition. Suitable shampoo compositions are generally comprised of from about 1-99%, preferably from about 5-95%, more preferably from about 10-90% by weight of the total composition of water, and from about 0.1-99%, preferably from about 1-95%, more preferably from about 5-90% by weight of the total composition of a cleansing surfactant. Suitable cleansing surfactants are generally anionic, amphoteric, betaine, or zwitterionic surfactants. Preferably, anionic surfactants include alkyl ether or alkyl ether sulfates such as sodium laureth-sulfate, sodium lauryl sulfate, and the like.

5. Conditioner Compartment

The kit may include at least one compartment containing a conditioner composition. Suitable conditioners generally contain from about 0.1-99%, preferably from about 0.5-95%, more preferably from about 1-90% by weight of the total composition of water and from about 0.1-99%, preferably from about 0.5-95%, more preferably from about 1-90% by weight of the total composition of cationic conditioning agents, e.g. cationic surfactants or cationic polymers. The conditioner may contain fatty acids or alcohols, silicone oils, and the like.

6. Post-Treatment Compartment

The kit may contain at least one compartment containing a post-treatment composition, in order to inhibit color fading and/or impart both shine- and condition-enhancing properties, wherein the post-treatment composition contains at least about 5% by weight of at least one oily component, based on the total weight of the post-treatment composition. Examples of such oily components include, but are not limited to those set forth below:

i) Silicones

Suitable as oily components are one or more silicones. Suitable silicones include volatile or nonvolatile nonionic silicone fluids, silicone resins, and silicone semi-solids or solids.

Volatile silicones are linear or cyclic silicones having a measurable vapor pressure, which is defined as a vapor pressure of at least 2 mm. of mercury at 20° C. Examples of volatile silicones are cyclic silicones having the general formula:

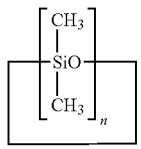

where n=3-7.

Also, linear volatile silicones that may be used in the compositions of the invention have the general formula:

$(CH_3)_3Si-O-[Si(CH_3)_2-O]_n-Si(CH_3)_3$ where n=0-7, preferably 0-5.

Also suitable are water insoluble nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

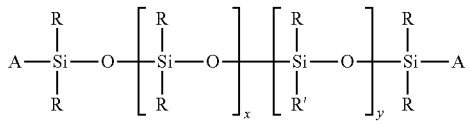

wherein R and R' are each independently alkyl, aryl, or an alkyl substituted with one or more amino groups, and x and y are each independently 0-100,000, with the proviso that x+y equals at least one and A is siloxy endcap unit. Polyalkylaryl siloxane fluids include, for example, polymethylphenylsiloxanes. These siloxanes are available, for example, from the General Electric Company as SF 1075 methyl phenyl fluid or from Dow Corning as 556 Cosmetic Grade Fluid.

Another type of silicone may also be a silicone polymer having the following general formula:

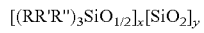

$[(RR'R'')_3SiO_{1/2}]_x[SiO_2]_y$ wherein R, R' and R'' are each independently a $C_{1-10}$ straight or branched chain alkyl or phenyl, and x and y are such that the ratio of x units to y units is 0.5 to 1 to 1.5 to 1.

ii) Organic Oils

Also suitable are various types of organic oils including esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like.

The organic oil may also comprise glyceryl esters of fatty acids, or triglycerides, such as castor oil, lanolin oil, triisocetyl citrate, $C_{10-18}$ triglycerides, caprylic/capric/triglycerides, coconut oil, mineral oil, almond oil, apricot kernel oil, avocado oil, babassu oil, evening primrose oil, *camelina sativa* seed oil, grape seed oil, *macadamia ternifolia* seed oil, corn oil, meadowfoam seed oil, mink oil, olive oil, palm kernel oil, safflower oil, sesame oil, soybean oil, sunflower oil, wheat germ oil, *camellia reticulata* seed oil and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the organic oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the oil are various fluorinated oils are fluoro guerbet esters or perfluoropolyethers.

Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

The post-treatment composition may also contain humectants, surfactants and conditioning agents such as those mentioned and listed for the pre-treatment composition of the present invention.

The post-treatment composition contains at least about 5% by weight, preferably at least about 10% by weight, preferably at least about 15% by weight, and more preferably at least about 20% by weight of at least one oily component, based on the total weight of the post-treatment composition.

According to one embodiment of the present invention, the post-treatment composition comprises at least about 20% in total by weight of one or more of the oily components as described above based on the total weight of the post-treatment composition.

According to another embodiment of the present invention, the post-treatment composition comprises at least about 10% in total by weight of one or more of the oily components as described above based on the total weight of the post-treatment composition.

II. Other Ingredients

The described embodiments of the present invention may also include one or more additional ingredients, which may be incorporated into the color altering composition, the developer composition, the pre-treatment composition, the shampoo composition, the conditioner composition, the post-treatment composition, or in all six compositions. Such ingredients include well-known conventional additives typically employed in hair coloring compositions such as basifying and acidifying agents, buffers, thickening agents, gelling agents, rheological modifiers, conditioning agents, surfactants, antioxidants, fragrances, and chelating agents.

The compositions of the present invention may also contain at least one conditioning agent. Such conditioning agents are typically chosen from synthetic oils such as polyolefins, plant oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds. Other useful conditioning agents are conditioning polymers which contain primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

The quaternized proteins are, in particular, chemically modified polypeptides bearing quaternary ammonium groups at the end of the chain or grafted onto the latter.

Among the polyamine, polyaminoamide or poly(quaternary ammonium) family of polymers, there may be mentioned:

1) Vinylpyrrolidone/dialkylaminoalkyl acrylate or methacrylate copolymers, quaternized or otherwise, such as the products sold by the company GAF CORPORATION under the name "GAFQUAT", for example "GAFQUAT 734 or 755", or alternatively the products designated "COPOLYMER 845, 958 and 937".
2) The cellulose ether derivatives containing quaternary ammonium groups, especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.
3) Cationic cellulose derivatives such as cellulose copolymers or cellulose derivatives grafted with a water-soluble quaternary ammonium monomer such as, for example hydroxyalkylcelluloses such as hydroxymethyl-, hydroxyethyl- or hydroxypropylcellulose with a methacryloylethyltrimethylammonium, methacrylamidopropyltrimethylammonium or dimethyldiallylammonium salt.
Marketed products corresponding to this definition are, more especially, the products sold by the company NATIONAL STARCH under the names "CELQUAT L 200" and "CELQUAT H 100".
4) The quaternized polysaccharides marketed under the name "JAGUAR C 13 S", sold by the company MEYHALL.
5) yclopolymers having a molecular weight of 20,000 to 3,000,000 such as, for example, the homopolymer of dimethyldiallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".
6) Quaternary polymers of vinylpyrrolidone and of vinylimidazole, such as, for example, the products marketed by the company BASF under the names "LUVIQUAT FC 905, FC 550 and FC 370".

Other conditioning polymers which are usable according to the invention are polyalkylenimines, especially polyethylenimines, polymers containing vinylpyridine or vinylpyridinium units, condensates of polyamines and epichlorohydrin, quaternary polyureylenes and chitin derivatives.

The cationic polysiloxanes such as those described in U.S. Pat. No. 4,185,087.

The conditioning polymers may also be chosen from amphoteric polymers, such as amphoteric polymers derived from chitosan or copolymers of diallyldialkylammonium and an anionic monomer.

Preferred polymers are, inter alia, polymers containing alkyl groups chosen from groups having 1 to 4 carbon atoms, and more especially methyl and ethyl groups.

Especially preferred conditioning polymers according to the invention are chosen from:

a) the poly(quaternary ammonium) polymers;
b) the copolymer of the diallyldimethylammonium chloride and acrylic acid (80/20) sold by the company CALGON under the name MERQUAT 280;
c) the homopolymer of dimethyldiallylammonium chloride sold by the company MERCK under the name MERQUAT 100;
d) the quaternized cellulose ether derivatives sold by the company UNION CARBIDE under the name JR;
e) the copolymer of vinylpyrrolidone and methacrylamidopropyltrimethylammonium chloride (85:15) sold by the company GAF under the name GAFQUAT HS 100;
f) the polymeric quaternary ammonium salt of acrylamide and beta-methacryloyloxyethyl trimethyl ammonium methosulfate, sold by the company, Nalco, under the names polyquaternium-5 or quaternium-39 or Merquat 5; and
g) the cationic polymers of the ionene type sold by the company Chimex, such as hexadimethrine chloride, also known as IONENE G.

According to a preferred embodiment, any of the compositions of the present invention may contain at least one conditioning agent as defined above, in an amount of from 0.01% to 12% by weight, preferably from 0.1 to 10% by weight, more preferably from 0.1 to 8% by weight, all weights being based on the total weight of each composition.

Suitable rheology modifying agents for use in the compositions of the present invention may include gelling and thickening agents such as the cellulosic thickeners, for example, hydroxyethylcellulose, hydroxypropylcellulose, and carboxymethylcellulose, guar gum and its derivatives, such as hydroxypropylguar, gums of microbial origin, such as xanthan gum and scleroglucan gum, and synthetic thickeners such as crosslinked homopolymers of acrylic acid and of acrylamidopropanesulphonic acid. Other rheology modifying agents include fatty acid amides such as coconut diethanolamide and monoethanolamide, and oxyethylenated monoethanolamide of carboxylic acid alkyl ether, and associative polymers. The associative polymers that may be used according to the present invention may be chosen from anionic, cationic, amphoteric, and nonionic polymers.

The anionic polymers may be chosen from crosslinked terpolymers of methacrylic acid, of ethyl acrylate, and of polyethylene glycol (10 EO) stearyl alcohol ether (Steareth-10), for example, those sold by the company Allied Colloids under the names Salcare SC 80 and Salcare SC 90, which are aqueous 30% emulsions of a crosslinked terpolymer of methacrylic acid, of ethyl acrylate and of steareth-10 allyl ether (40/50/10).

Other non-limiting examples of commercial products corresponding to the anionic polymers include the products sold by the company Goodrich under the trade names Pemulen TR1, Pemulen TR2, and Carbopol 1382 and the product sold by the company SEPPIC under the name Coatex SX. In at least one embodiment, the polymer is Pemulen TR1.

Other examples of anionic polymers are maleic anhydride/C 30-C 38 alpha-olefin/alkyl maleate terpolymers, such as the product (maleic anhydride/C 30-C 38 alpha-olefin/isopropyl maleate copolymer) sold under the name Performa V 1608 by the company Newphase Technologies and acrylic terpolymers such as a methacrylic acid/methyl acrylate/behenyl alcohol dimethyl-meta-isopropenylbenzylisocyanate ethoxylated (40 EO) terpolymer, as an aqueous 25% dispersion.

Another type of anionic polymers include copolymers comprising among their monomers a carboxylic acid containing alpha, beta-monoethylenic unsaturation and an ester of a carboxylic acid containing alpha, beta-monoethylenic unsaturation and of an oxyalkylenated fatty alcohol. A non-limiting example of a compound of this type is Aculyn 22 sold by the company Rohm and Haas, which is a methacrylic acid/ethyl acrylate/stearyl methacrylate oxyalkylenated terpolymer.

Cationic associative polymers may include, but are not limited to:

(I) cationic associative polyurethanes which may be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes which can be used according to the present invention" encompasses these three types of polymer, namely polyurethanes per se, polyureas and polythioureas, and also copolymers thereof. Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate.

(II) quaternized cellulose derivatives and polyacrylates containing non-cyclic amine side groups. The quaternized cellulose derivatives may include, for example:

quaternized celluloses modified with groups comprising at least one fatty chain, such as alkyl, arylalkyl, and alkylaryl groups comprising at least 8 carbon atoms, and mixtures thereof; and quaternized hydroxyethylcelluloses modified with groups comprising at least one fatty chain, such as alkyl, arylalkyl, and alkylaryl groups comprising at least 8 carbon atoms, and mixtures thereof.

The alkyl radicals borne by the above quaternized celluloses or hydroxyethylcelluloses may comprise from 8 to 30 carbon atoms. In at least one embodiment, the aryl radicals may be chosen from phenyl, benzyl, naphthyl, and anthryl groups.

Examples of quaternized alkylhydroxyethylcelluloses containing C 8-C 30 fatty chains include, for instance, the products Quatrisoft LM 200, Quatrisoft LM-X 529-18-A, Quatrisoft LM-X 529-18B (C 12 alkyl), and Quatrisoft LM-X 529-8 (C 18 alkyl) sold by the company Amerchol, and the products Crodacel QM, Crodacel QL (C 12 alkyl) and Crodacel QS (C 18 alkyl) sold by the company Croda.

The amphoteric associative polymers may be chosen, for example, from those comprising at least one non-cyclic cationic unit. The amphoteric associative polymers according to the present invention may be chosen from acrylic acid/(meth)acrylamidopropyltrimethyl-ammonium chloride/stearyl methacrylate terpolymers.

The nonionic associative polymers that may be used according to the present invention may be chosen from:

(1) celluloses modified with groups comprising at least one fatty chain; for example:

hydroxyethylcelluloses modified with groups comprising at least one fatty chain, such as alkyl, arylalkyl, and alkylaryl groups, and mixtures thereof, and in which the alkyl groups are, for example, C 8-C 22, for instance the product Natrosol Plus Grade 330 CS (C 16 alkyls) sold by the company Aqualon, and the product Bermocoll EHM 100 sold by the company Berol Nobel, those modified with alkylphenyl polyalkylene glycol ether groups, such as the product Amercell Polymer HM-1500 (nonylphenyl polyethylene glycol (15) ether) sold by the company Amerchol.

(2) hydroxypropyl guars modified with groups comprising at least one fatty chain, such as the product Esaflor HM 22 (C 22 alkyl chain) sold by the company Lamberti, and the products RE210-18 (C 14 alkyl chain) and RE205-1 (C 20 alkyl chain) sold by the company Rhone-Poulenc.

(3) copolymers of vinylpyrrolidone and of fatty-chain hydrophobic monomers; for example:

the products Antaron V216 or Ganex V216 (vinylpyrrolidone/hexa-decene copolymer) sold by the company I.S.P.

the products Antaron V220 or Ganex V220 (vinylpyrrolidone/eicosene copolymer) sold by the company I.S.P.

(4) copolymers of C 1-C 6 alkyl methacrylates or acrylates and of amphiphilic monomers comprising at least one fatty chain, for example, the oxyethylenated methyl acrylate/stearyl acrylate copolymer sold by the company Goldschmidt under the name Antil 208.

(5) copolymers of hydrophilic methacrylates or acrylates and of hydrophobic monomers comprising at least one fatty chain, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix compounds sold by the company Sud-Chemie.

In at least one embodiment, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In another embodiment, it is possible for at least one pendent chain to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These polymers may also be chosen from graft polymers and star-burst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers may comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

Examples of nonionic fatty-chain polyurethane polyethers that may be used include Rheolate 205 containing a urea function, sold by the company Rheox, Rheolate 208, 204, and 212, and also Acrysol RM 184.

Polyurethanes may also be chosen, for example, from the product Elfacos T210 containing a C 12-14 alkyl chain, and the product Elfacos T212 containing a C 18 alkyl chain, from Akzo.

The product DW 1206B from Rohm and Haas containing a C 20 alkyl chain and a urethane linkage, sold at a solids content of 20% in water, may also be used.

It is also possible to use solutions or dispersions of these polymers, for example, in water or in aqueous-alcoholic medium. Examples of such polymers include, but are not limited to, Rheolate 255, Rheolate 278 and Rheolatee 244 sold by the company Rheox, and the products DW 1206F and DW 1206J sold by the company Rohm and Haas.

In at least one embodiment, the polyurethane polyether may be chosen from those that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm and Haas under the names Aculyn 44 and Aculyn 46 [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

The rheology-modifying agents may be used in any of the compositions of the present invention, for example, in concentrations ranging from about 0.1% to about 10.0% by weight, preferably from about 0.5% to about 5.0% by weight, even more preferably from about 1.0% to about 4.0% by weight of the total weight of each composition.

III. Methods of Treatment

In the method of the invention the pre-treatment composition is applied to the hair. The color-altering composition comprising a dye material or bleaching material is combined with the developer composition in the developer compartment. The mixture is then applied to the pretreated hair. The mixture may be applied to saturate the hair, provide highlights, touch-up the roots, or in any other manner the user prefers. The mixture is left in the hair for about 5-60 minutes, or as recommended in the instructions given in the kit.

After the indicated amount of time has elapsed, the mixture is rinsed off the hair with water. Thereafter, a shampoo composition is applied to the hair for a period of time ranging from about 15 seconds to 5 minutes. The shampoo composition is rinsed from the hair using water. A conditioner composition is then applied to the hair for a period of time ranging from about 1-10 minutes. The conditioner composition is rinsed from the hair using water. Finally, the post-treatment composition is applied to the hair and may or may not be rinsed off. Following the application of the post-treatment composition, the hair may be styled as desired.

The shampoo, conditioner, and post-treatment compositions are provided in the kit such that they may be used on a daily or weekly basis, depending on the needs of the consumer. Preferably, the shampoo and conditioner compositions are used on a weekly to bi-weekly basis, and the post-treatment composition is used on a daily basis.

IV. Testing Results and Examples

Focus group studies were conducted with consumers of hair color after their in-home use of the inventive hair color system comprising a pre-treatment composition (before coloration), an oxidative dye composition, a developer composition, a shampoo (weekly use), a conditioner (weekly use) and a post-treatment composition (daily use). Their comments are shown below:

| Color System and Components | Summary of Comments |
|---|---|
| Pre-treatment composition | Positive appearance of hair and good feel of the hair after coloration attributed to the pre-treatment by the consumers |
| Shampoo and conditioner | Consumers appeared to like the idea of having a shampoo and conditioner built into a hair color system |
| Post-treatment composition | Good shine benefits to hair |
| Hair color system | Unique and interesting complete and full color and care system for in-home use; Overall good conditioning (softer, silk, healthier) and shine benefits to hair which are just as good or even better than having hair colored in a salon; acceptable and/or better purchase price on a multi-component system compared to the cost of having hair colored in a salon; satisfactory or better hair color; Short processing time (about 30 minutes) |

The comments in the table above show that the color and care system of the present invention is able to provide the consumers with a method of treating and coloring hair at home that imparts desirable conditioning and shine benefits to hair and good color coverage while at the same time, presenting an affordable alternative to having hair colored in a salon. This system also provides the consumer with a way to maintain the color and the good condition of the hair in a convenient and inexpensive manner.

Formulation Examples

| Ingredient | % level |
|---|---|
| Pre-treatment Composition | |
| conditioning agents | 0.5 |
| Hair conditioning agents such as hydrolyzed oats, hydrolyzed wheat protein, hydrolyzed keratin, ceramide | 0.1% |
| humectants such as glycerin, propylene glycol | 3 |
| fatty alcohol | 3.2 |
| alkoxylated alcohol | 0.8 |
| alkanolamide or other viscosity modifiers | 1.2 |
| preservatives, fragrance, | up to 2% in total |
| Q.S. Water | 100 |

-continued

| Ingredient | % level |
|---|---|
| Post-treatment Composition | |
| esters | 6 |
| conditioning agents | 0.5 |
| cyclopentasiloxane | 14.5 |
| amodimethicone | 0.3 |
| phenyl trimethicone | 5 |
| filmforming agents | 2% |
| PEG/PPG-8/14 dimethicone, polysorbate 20, poloxamer 407 | up to 2.4% in total |
| alkoxylated alcohols | 2% |
| preservatives, fragrance, chelants | up to 2% in total |
| Q.S. Water | 100 |

The hair color-altering, developer, shampoo and conditioner compositions may be based on standard formulations known to persons of ordinary skills in hair color and hair care formulation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating the hair, comprising:
    a) applying to the hair a pre-treatment composition comprising a humectant and at least one conditioning agent;
    b) combining a color-altering composition and a developer composition to form a mixture;
    c) applying the mixture onto the hair;
    d) removing said mixture from the hair;
    e) washing the hair with a shampoo composition;
    f) conditioning the hair with a conditioner composition; and,
    g) applying a post-treatment composition onto the hair in order to inhibit color fading and/or impart both shine- and condition-enhancing properties, and wherein the post-treatment composition contains at least one conditioning agent and at least about 5% by weight of at least one oily component, based on the total weight of the post-treatment composition wherein said at least one oily component is selected from the groups consisting of silicones, organic oils, synthetic oils and mixture thereof.

2. The method of claim 1, wherein said color-altering composition comprises a hair dye material and a bleaching material.

3. The method of claim 2, wherein said hair dye material is chosen from primary intermediates, couplers and mixtures thereof.

4. The method of claim 1, wherein said color-altering composition further comprises at least one rheological modifying agent.

5. The method of claim 4, wherein said at least one rheological modifying agent is an associative polymer chosen from anionic polymers, cationic polymers, amphoteric polymers, nonionic polymers, and mixtures thereof.

6. The method of claim 1, wherein said pre-treatment composition comprises a humectant chosen from glycerin, propylene glycol, butylene glycol, ethylene glycol, polyethylene glycols having from 4 to 250 repeating ethylene glycol units, ethoxydiglycol, and mixtures thereof.

7. The method of claim 1, wherein said at least one conditioning agent in the pre-treatment composition, is chosen from cationic quaternary ammonium compounds, cationic polymers, and mixtures thereof.

8. The method of claim 1, wherein said at least one conditioning agent in the pre-treatment composition, is chosen from synthetic oils, natural oils, esters, fatty amines, alkanolamides, fatty acids, ceramides, and mixtures thereof.

9. The method of claim 1, wherein said at least one conditioning agent in the post-treatment composition, is chosen from cationic quaternary ammonium compounds, cationic polymers, and mixtures thereof.

10. The method of claim 1, wherein said at least one conditioning agent in the post-treatment composition, is chosen from synthetic oils, natural oils, esters, fatty amines, alkanolamides, fatty acids, ceramides, and mixtures thereof.

11. The method of claim 1, wherein the at least one oily component in the post-treatment composition is a silicone chosen from volatile silicones, nonvolatile silicones, silicone resins, silicone oils, and mixtures thereof.

12. The method of claim 1, wherein the at least one oily component in the post-treatment composition is chosen from esters, triglycerides, mineral oil, glyceryl esters, plant oils, hydrocarbon oils, lanolin derivatives, sorbitan derivatives, fluorinated oils, castor oils, and mixtures thereof.

13. The method of claim 1, wherein said shampoo composition is applied to the hair on a weekly to bi-weekly basis following initial treatment of the hair.

14. The method of claim 1, wherein said conditioner composition is applied to the hair on a weekly to bi-weekly basis following initial treatment of the hair.

15. The method of claim 1, wherein said post-treatment composition is applied to the hair on a daily basis following initial coloration of the hair.

16. A hair care kit, comprising:
    a) a compartment containing a pre-treatment composition comprising a humectant and at least one conditioning agent;
    b) a compartment containing a color-altering composition;
    c) a compartment containing a developer composition;
    d) a compartment containing a shampoo composition;
    e) a compartment containing a conditioner composition; and,
    f) a compartment containing a post-treatment composition, wherein the post-treatment composition contains at least one conditioning agent and at least about 5% by weight of at least one oily component, based on the total weight of the post-treatment composition wherein said at least one oily component is selected from the groups consisting of silicones, organic oils, synthetic oils and mixture thereof.

* * * * *